United States Patent [19]

Matkovich et al.

[11] Patent Number: 5,364,526
[45] Date of Patent: Nov. 15, 1994

[54] SYSTEM FOR PROCESSING SEPARATE CONTAINERS OF BIOLOGICAL FLUID

[75] Inventors: Vlado I. Matkovich, Glen Cove; Thomas J. Bormann, Melville; Thomas C. Gsell; Frank R. Pascale, both of Glen Cove, all of N.Y.

[73] Assignee: Pall Corporation, Glen Cove, N.Y.

[21] Appl. No.: 107,033

[22] Filed: Aug. 17, 1993

Related U.S. Application Data

[63] Continuation of Ser. No. 795,480, Nov. 21, 1991, abandoned.

[51] Int. Cl.⁵ .................. B01D 36/00; B01D 61/00
[52] U.S. Cl. ..................... 210/206; 210/188; 210/257.1; 210/258; 604/410; 149/105
[58] Field of Search ............... 210/188, 206, 257.1, 210/258, 435, 436, 446, 492; 55/467; 96/155; 422/101, 102; 141/67, 105, 107, 309; 604/4, 30, 122, 123, 126, 410

[56] References Cited

U.S. PATENT DOCUMENTS

| | | | |
|---|---|---|---|
| 2,781,064 | 2/1957 | Dawkins | 141/309 |
| 3,000,540 | 9/1961 | Wheeler | 141/309 |
| 3,631,654 | 1/1972 | Riely | 55/524 |
| 3,650,093 | 3/1972 | Rosenberg . | |
| 3,941,126 | 3/1976 | Dietrich et al. | 141/107 |
| 4,126,558 | 11/1978 | Luceyk | 210/429 |
| 4,191,183 | 3/1980 | Mendelson | 141/107 |
| 4,276,170 | 6/1981 | Vaillancourt | 210/436 |
| 4,360,435 | 11/1982 | Bellamy et al. | 210/636 |
| 4,372,100 | 2/1983 | Miller et al. | 141/105 |
| 4,459,139 | 7/1984 | vonReis et al. . | |
| 4,507,119 | 3/1985 | Spencer | 604/280 |
| 4,680,025 | 7/1987 | Kruger et al. | 604/6 |
| 4,701,267 | 10/1987 | Watanabe et al. | 210/491 |
| 4,857,190 | 8/1989 | Wada et al. | 210/232 |
| 4,922,975 | 5/1990 | Polaschegg | 141/105 |
| 4,963,260 | 10/1990 | Naoi et al. | 210/446 |
| 4,985,153 | 1/1991 | Kuroda et al. | 210/782 |
| 5,056,568 | 10/1991 | DiGianfilippo et al. | 141/1 |
| 5,074,839 | 12/1991 | Choksi et al. | 604/4 |
| 5,098,371 | 3/1992 | Juji et al. | 604/410 |
| 5,100,564 | 3/1992 | Pall et al. | 210/782 |
| 5,126,054 | 6/1992 | Matkovich | 210/641 |
| 5,217,627 | 6/1993 | Pall et al. | 210/767 |

FOREIGN PATENT DOCUMENTS

| | | |
|---|---|---|
| 2012677 | 9/1990 | Canada . |
| 0155003 | 9/1985 | European Pat. Off. . |
| 0446713 | 9/1991 | European Pat. Off. . |
| 0455215 | 11/1991 | European Pat. Off. ........ A61J 1/05 |
| 9117809 | 11/1991 | WIPO . |

Primary Examiner—Robert A. Dawson
Assistant Examiner—Sun Uk Kim
Attorney, Agent, or Firm—Leydig, Voit & Mayer

[57] ABSTRACT

Processes and systems for combining multiple units of a biological fluid in independent containers into a single container are disclosed.

8 Claims, 1 Drawing Sheet

SYSTEM FOR PROCESSING SEPARATE CONTAINERS OF BIOLOGICAL FLUID

This application is a continuation of application Ser. No. 07/795,480, filed Nov. 21, 1991 now abandoned.

TECHNICAL FIELD

This invention relates to a system, apparatus, and method for processing separate containers of biological fluid.

BACKGROUND OF THE INVENTION

The development of plastic blood collection bags in the 1960's facilitated the separation of donated whole blood into its various components, thereby making platelet concentrate (PC) available as a transfusion product. A typical unit of random-donor PC is about 50 ml, and is typically produced from a unit of whole blood, which is about 450 ml in United States practice, by differential sedimentation.

The need for specific blood components is growing rapidly as the therapeutic administration of these components increases. The net result is twofold: biological fluids are increasingly important, and the need to maximize yield has increased. Thus, any amount that is retained in the processing system, or is recovered but is not viable and physiologically active, represents a potentially significant loss. While the failure to maximize yield is a serious concern with respect to all blood components, it is particularly applicable to the production of PC, since typical procedures for processing platelet containing solutions such as PC fail to efficiently maximize platelet recovery.

Maximizing recovery of platelets or a platelet concentrate after processing may be adversely affected in several ways. For example, platelets are notorious for being "sticky", an expression reflecting the tendency of platelets suspended in blood plasma to adhere to any non-physiological surface (e.g., the surfaces of the components of a system for processing biological fluid) to which they are exposed. Under many circumstances, they also adhere strongly to each other.

As detailed in U.S. Pat. No. 4,880,548, which discloses methods and devices for leucocyte depleting blood components, including PC, there will be substantial contact between platelets and the internal surfaces of the leucocyte depletion device. It is therefore desirable that the leucocyte depletion device should minimize platelet loss due to that contact and should not adversely affect platelet viability or physiological activity.

This problem is magnified when multiple units of platelet containing solutions are pooled or processed. When multiple units of PC from random donors are pooled for transfusion into a patient, some of the fluid is trapped or retained in the individual collection and processing assemblies, collectively representing a significant loss if the highly valuable fluid can not be recovered.

In view of this, there is a growing need for a system and method for economically and efficiently processing a biological fluid, such as a platelet containing solution, that will not only pool large amounts (e.g. multiple units) of the fluid, but will also leucocyte deplete the fluid and maximize the recovery of platelets.

DEFINITIONS

The following definitions are used in reference to the invention:

(A) Biological Fluid: Biological fluid includes any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate (PC), platelet-rich plasma (PRP), platelet-free plasma, platelet-poor plasma, plasma, or packed red cells (PRC); analogous blood products derived from blood or a blood component or derived from bone marrow; red cells separated from plasma and resuspended in physiological fluid; and platelets separated from plasma and resuspended in physiological fluid. The biological fluid may include leucocytes, or may be treated to remove leucocytes. As used herein, biological fluid refers to the components described above, and to similar blood products obtained by other means and with similar properties.

(B) Unit of PC or platelets: As used herein, a "unit" is defined in the context of United States practice, and a unit of PC or of platelets in physiological fluid or plasma, is the quantity derived from one unit of whole blood. Typically, the volume of a unit varies. Multiple units of platelets may be pooled or combined, typically by combining four or more units.

(C) Porous medium: A porous medium is one through which one or more biological fluids pass. The porous medium for use with biological fluids may be formed from any natural or synthetic fiber or from a porous or permeable membrane (or from other materials of similar surface area and pore size) compatible with biological fluid (e.g., blood or a blood component). The surface of the fibers or membrane may be unmodified or may be modified to achieve a desired property. For example, the medium may be subjected to gas plasma treatment, preferably in order to reduce platelet adhesion.

Although the porous medium may remain untreated, the fibers or membrane are preferably treated in order to reduce or eliminate platelet adherence to the medium. Any treatment which reduces or eliminates platelet adhesion is included within the scope of the present invention. For example, the fibers may be surface modified as disclosed in U.S. Pat. No. 4,880,548, in order to increase the critical wetting surface tension (CWST) of the fibers and to be less adherent of platelets. Defined in terms of CWST, a preferred range of CWST for a porous medium according to the invention is above about 70 dynes/cm, more preferably above about 90 dynes/cm.

The porous medium may be pre-formed, multi-layered, and/or may be treated to modify the fiber surfaces either before or after forming the fibrous lay-up. The porous medium may be configured in any suitable fashion, such as a flat sheet, a corrugated sheet, a web, hollow fibers, or a membrane.

SUMMARY OF THE INVENTION

Processes and systems according to the invention include a manifold assembly for combining multiple units of a biological fluid in independent containers into a single container. Processes and systems according to the invention may also include a leucocyte depletion assembly.

Additionally, processes and systems according to the invention may include a gas inlet and/or a gas outlet that maximizes the recovery of a biological fluid that may be entrapped or retained during processing; the processes and systems may also include a drip chamber that collects gas and/or controls the rate of flow of a biological fluid through the system.

The processes and systems of the present invention provide for increased yield of a biological fluid, since valuable fluid that would normally be retained in various elements of a biological fluid processing system may now be recovered. The present invention also provides for reduced processing time and operator labor.

BRIEF DESCRIPTION OF THE FIGURE

The FIGURE is an embodiment of a biological fluid processing system comprising a manifold assembly according to the invention.

SPECIFIC DESCRIPTION OF THE INVENTION

Figure 1:
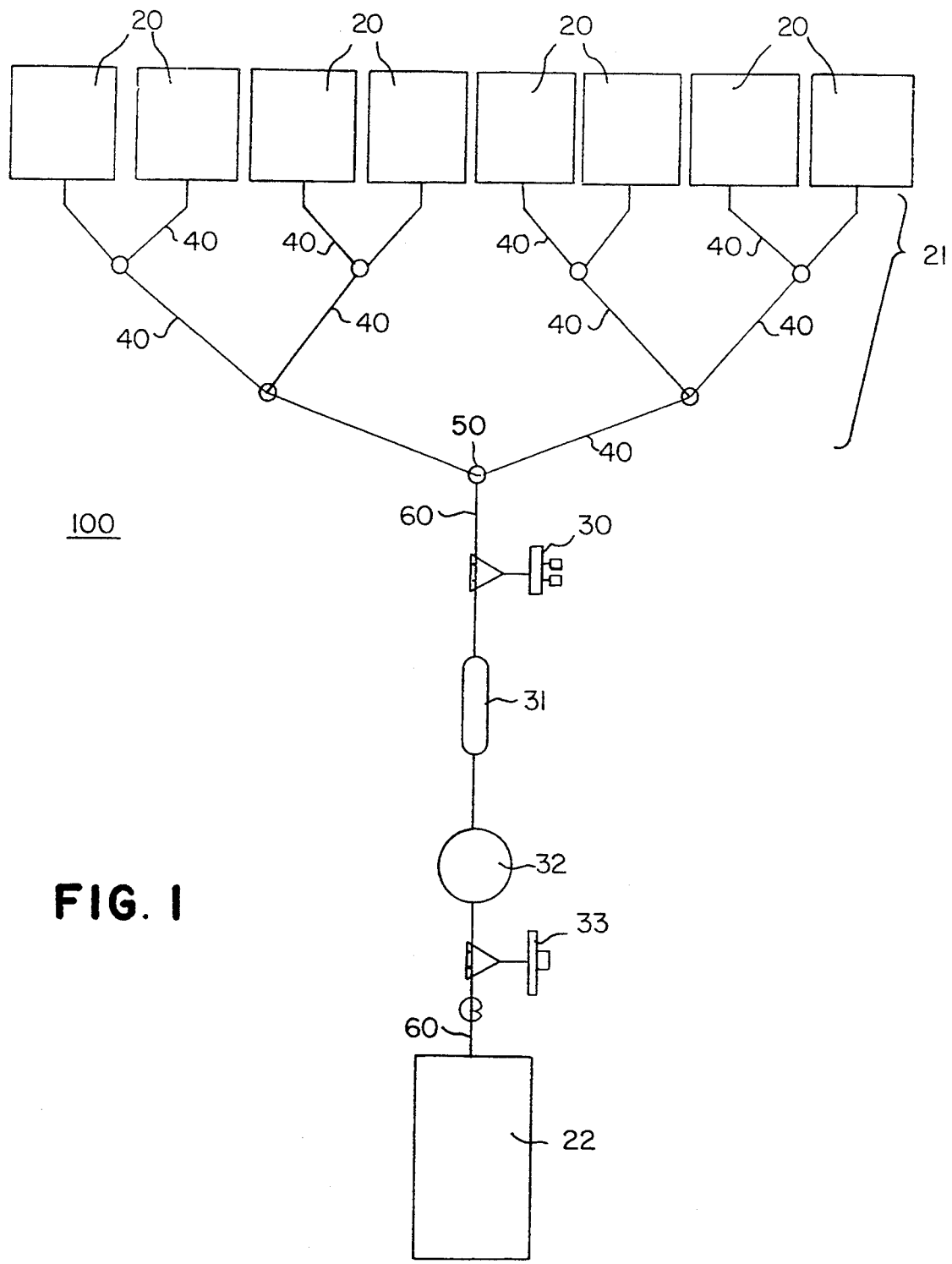

In accordance with the present invention, units of biological fluid, particularly PC, which are in separate source containers, are passed through a biological fluid processing system which maximizes recovery of the biological fluid into a single receiving container. The processing system may also include a leucocyte depletion assembly that is interposed between the source containers and the receiving container.

An exemplary biological fluid processing system is shown in the FIGURE. Manifold assembly 100 may include containers 20, each suitable for holding at least one unit of a biological fluid such as PC, in fluid communication with a pooling assembly 21. In the illustrated embodiment, the pooling assembly 21 includes a network or plurality of conduits 40 that converge into a single conduit 60 at outlet or junction 50. Some of the conduits 40 function as inlets from the source containers 20. Alternatively, pooling assembly 21 may include a housing having at least two inlets and an outlet. The outlet or junction 50 of the pooling assembly 21 is in fluid communication with a receiving or transfer container 22. In the illustrated embodiment, fluid communication with the receiving container 22 is preferably established by a conduit 60. Interposed in the conduit 60 between the outlet or junction 50 and the container 22 may be at least one device or assembly. For example, as shown in the illustrated embodiment, the manifold assembly 100 may include a gas inlet 30, a drip chamber 31, a leucocyte depletion assembly 32, and a gas outlet 33.

Each of the components of the invention will now be described in more detail below.

The source and receiving containers which are used in the biological fluid processing assembly may be constructed of any material compatible with biological fluids. A wide variety of these containers are already known in the art. For example, blood collection and satellite bags are typically made from plasticized PVC, e.g. PVC plasticized with dioctylphthalate, diethylhexylphthalate, or trioctyltrimellitate. The bags may also be formed from a polyolefin, polyurethane, polyester, or a polycarbonate.

The pooling assembly of the instant invention provides fluid communication between at least two source containers and a receiving container, preferably by channeling multiple flow paths into a single flow path. As illustrated in the FIGURE, the pooling assembly 21 preferably comprises a plurality of conduits 40 and an outlet or junction 50. Although the conduits can be configured in a number of ways, the pooling assembly preferably comprises a network or tiered arrangement of conduits 40, preferably including one or more junctions, such as one or more Y-connectors. As used herein, the conduits provide fluid communication between the source of the biological fluid, such as separate unit containers 20, and a multiple unit container, such as transfer or receiving container 22. A clamp, seal, valve, transfer leg closure, or the like, may be located within or on at least one of the conduits.

Alternatively, the pooling assembly 21 may include at least one device having multiple inlets and a single outlet in fluid communication with junction 50.

The pooling assembly used in the instant invention may be constructed of any material compatible with a biological fluid. For example, the pooling assembly may be composed of a non-flexible material, for example, acrylonitrile butadiene styrene (ABS), polycarbonate, or stainless steel. Alternatively, it may be composed of a flexible material, such as polyvinyl chloride (PVC), or plasticized PVC, e.g., PVC plasticized with dioctylphthalate, diethylhexylphthalate, or trioctyltrimellitate.

In accordance with another embodiment of the invention, the biological fluid processing system may include a drip chamber 31. As noted in more detail below, drip chamber 31 may be used to prevent gas from reaching a leucocyte depletion assembly 32 and/or the receiving container 22 downstream of the drip chamber, and for maximizing recovery of the biological fluid.

The drip chambers which may be used in the biological fluid processing assembly may be constructed of any material compatible with biological fluid and gas. Furthermore, the drip chamber may include at least one porous element, preferably a liquophobic porous membrane, that allows gas into and/or out of a biological fluid processing system, but resists the passage of biological fluid. The porous element may be positioned in a conduit, or, more preferably, it may be included in a housing of the drip chamber. Further, the surface of the element may be oriented in a variety of ways with respect to the flow of the biological fluid. For example, two porous elements may be placed at opposite ends or sides of the drip chamber, or a single element may be offset within the drip chamber.

The leucocyte depletion assembly 32 comprises at least one porous medium which removes leucocytes from the biological fluid. Exemplary leucocyte depletion media for use with a biological fluid such as PC is disclosed in U.S. Pat. No. 4,880,548. The leucocyte depletion assembly 32 may be positioned in the manifold assembly in a variety of ways. For example, it may be located downstream of the outlet of the pooling assembly 50 and the drip chamber 31.

A plurality of leucocyte depletion assemblies may be used in connection with the pooling assembly of the instant invention. For example, a plurality of leucocyte depletion assemblies may placed in a plurality of pooling assembly inlets, i.e., in direct communication with the individual source containers of biological fluid. Alternatively, a plurality of leucocyte depletion assemblies may be placed more downstream in the pooling assembly, i.e., at similar or different tiers of the pooling assembly. In a preferred embodiment, a leucocyte depletion assembly 32 is interposed between the source containers 20 and the receiving container 22, for example, in conduit 60.

In another embodiment, a gas inlet and/or a gas outlet may be used to maximize the recovery of biological fluid in receiving or transfer container 22. Preferably, the gas inlet 30 and the gas outlet 33 may be, respectively, upstream and downstream of the leucocyte depletion assembly 32. More preferably, as exemplified in the FIGURE, the gas inlet 30 is downstream of the outlet of the pooling assembly 50 and upstream of the drip chamber 31, which is upstream of the leucocyte depletion assembly 32, while the gas outlet 33 is downstream, interposed between the leucocyte depletion assembly 32 and the receiving or transfer container 22. Alternatively, a gas inlet and/or a gas outlet may be positioned in a drip chamber, a conduit, or the receiving and/or source containers.

The gas inlet is a porous element which allows gas into a biological fluid processing system. Thus, the gas inlet may provide for increasing the recovery of a valuable biological fluid (e.g., PC) that may otherwise be retained in various components of the manifold assembly during processing and would otherwise be lost.

The gas outlet is a porous element which allows gas that may be present in a biological fluid processing system out of the system. Thus, the gas outlet may provide for minimizing the volume of gases that remain in, or in contact with, a biological fluid during processing. The gas outlet may also allow gas into the biological fluid processing system.

The gas inlet and gas outlet should be chosen so that the sterility of the system is not compromised.

The gas inlet and gas outlet each comprise at least one porous element designed to allow gas to pass therethrough. A variety of materials may be used, provided the requisite properties of the porous element are achieved. These properties include the necessary strength to handle the differential pressures encountered in use and the ability to provide the desired filtration capability while providing the desired permeability without the application of excessive pressure. In a closed system, the porous elements of the gas inlet and the gas outlet should also preferably have a pore rating of about 0.2 micrometer or less to preclude bacteria entering the system.

Preferably, the gas inlet and gas outlet include at least one liquophobic porous element. Because the liquophobic porous element is not wettable, or poorly wettable, by the biological fluid being processed in the system, gas in the system that contacts the liquophobic element will pass through it, while the biological fluid will not. The gas outlet may also include at least one liquophilic porous element, that allows gas to exit, but not enter, the system. In a preferred embodiment of the invention, the gas outlet includes both a liquophobic membrane and a liquophilic membrane. Additionally, the gas inlet and/or the gas outlet may be included in a housing, which may include a cap or closure. Exemplary gas inlets and gas outlets and processes for using them are as disclosed in PCT/US91/03616, filed 24 May 1991.

As noted above, the placement of the gas inlet and/or the gas outlet may be optimized to achieve a desired result. For example, the gas inlet 30 may be located as far upstream of the manifold outlet or junction 50 as is practical in order to sufficiently maximize the recovery of biological fluid from the manifold assembly 100. Thus, gas inlets may be located in each of the source containers 20 of the biological fluid to be pooled. Alternatively, the gas inlet 30 may be placed in a conduit 40 or downstream of the outlet or junction 50 of the pooling assembly 21.

Also, it may be desirable to locate the gas outlet 33 in conduit 60 downstream of the outlet or junction 50 and as close to receiving or transfer container 22 as is possible in order to maximize the volume of gas that is removed from the manifold assembly 100. Alternatively, the gas outlet may be located in the receiving or transfer container 22 itself. The gas inlet or the gas outlet may be located in the drip chamber 31. In a preferred embodiment of the invention, a gas inlet and/or a gas outlet may be interposed between the source containers 20 and the receiving container 22, for example, in conduit 60.

Included within the scope of the invention is the use of more than one gas inlet and/or gas outlet. For example, when the pooling assembly includes a plurality of leucocyte depletion assemblies, the pooling assembly may also include a plurality of gas inlets and/or gas outlets in any of the containers, or in any of the conduits communicating with the leucocyte depletion assemblies.

A method according to the invention may be described with reference to the FIGURE, where the components are shown in a preferably vertical arrangement, with the source containers 20 at the highest point. Biological fluid, as used hereinafter, PC, in a plurality of containers 20 passes through the conduits of the pooling assembly 21 and through outlet or junction 50 to receiving or transfer container 22. As the PC flows, it preferably contacts at least one device, assembly, or porous element, e.g., a gas inlet 30, a drip chamber 31, or a gas outlet 33, for preventing gas from reaching a leucocyte depletion assembly or the receiving container, and for maximizing the recovery of the PC, which is interposed between the source containers 20 and the receiving or transfer container 22. In accordance with the present invention, the PC may also pass through at least one leucocyte depletion assembly 32 which is interposed between the source containers 20 and the receiving or transfer container 22.

In order to maximize recovery of PC prior to processing, air or gas may be introduced into the source containers 20 through the gas inlet assembly 30 or the gas outlet assembly 33, preferably by using a syringe (not shown). As used herein, air or gas refers to any gaseous fluid, such as sterilized air, oxygen, carbon dioxide, and the like; it is intended that the invention not be limited to the type of gas used. While the introduced fluid is preferably ambient air or a sterile gas, some non-gaseous fluids may also be suitable. For example, fluid that is lighter than the biological fluid and is non-reactive with it is included within the scope of the present invention.

Introducing gas into the source containers 20 may be accomplished by opening a flow path from the gas inlet 30 or the gas outlet 33 to the appropriate source container 20, while closing the flow path to the receiving or transfer container 22. For example, the clamps on the conduits leading to the receiving or transfer container 22 and all but one container 20 may be closed, so that when gas is introduced into the system, gas in the conduit will enter the open container. In a preferred embodiment, the process includes introducing gas sequentially into the source containers 20. The flow path to each source container may be closed after gas has been introduced into that container.

The flow path to the first source container 20 is then opened, and as the PC passes from the first source container 20, and flows through the pooling assembly 21 toward receiving or transfer container 22, it displaces the gas that was ahead of the column of flowing PC; this gas is exhausted or removed from the system. The gas may be vented from the system through a porous element in the drip chamber or in the conduit, or preferably, through an open gas outlet 33. Once the gas has been exhausted from the system, the gas outlet may be inactivated to prevent gas from entering the system. For example, the gas outlet may be inactivated by manually closing the outlet, e.g., by capping or clamping. Preferably, the gas outlet includes a liquophobic element, and more preferably, both a liquophobic element and a liquophilic element, which inactivates the outlet automatically, upon wetting by the PC.

Once the gas ahead of the PC column has been exhausted and the flow of PC has stopped, clamps adjacent to the other source containers are opened, preferably, sequentially, so that PC from the other containers 20 may pass through the pooling assembly 21 toward the receiving or transfer container 22. The clamp adjacent to the receiving or transfer container 22 is opened so that the PC can flow into the container 22. Preferably, the clamp adjacent to the receiving or transfer container 22 is opened before the clamps adjacent to the other source containers are opened.

Initiating the flow of PC from the other source containers also displaces gas ahead of the other units of PC. Preferably, this gas may be collected in drip chamber 31 interposed between the outlet or junction 50 and the receiving or transfer container 22. Passing the PC through a drip chamber 31 may include collecting gas and/or controlling the rate of flow of the PC. The drip chamber 31 is typically inverted until the PC fills the drip chamber, at which point the drip chamber is returned to its normal orientation.

In accordance with the invention, the PC may also be passed through a leucocyte depletion assembly 32 interposed between the outlet or junction 50 of the manifold assembly 21 and the receiving or transfer container 22. Preferably, the leucocyte depletion assembly 32 is located between the gas inlet 30 and the gas outlet 33. An exemplary process for passing the PC through a leucocyte depletion assembly is disclosed in U.S. Pat. No. 4,880,548.

As the PC passes through the drip chamber 31 and the optional leucocyte depletion assembly 32, the gas ahead of the PC may be exhausted through the gas outlet 33 as described previously. Pooled PC is then recovered in the receiving or transfer container 22 and, in accordance with the invention, the introduction of air or gas into the receiving container is eliminated or minimized, so the PC is recovered without collecting air.

In order to maximize recovery of PC, gas may be introduced behind the PC retained in the system. The gas that was initially introduced into the source containers 20 through either the gas inlet 30 or the gas outlet 33 will follow the PC as it flows through the conduits. This increases the recovery of the PC, since the gas following the PC "chases" the fluid from the conduits. Furthermore, after the PC has passed through the pooling assembly into the receiving or transfer container 22 and the source containers 20 have collapsed, gas may be introduced behind the retained PC by opening gas inlet 30. Additional PC may then be recovered in the receiving or transfer container 22.

Once recovery of PC has been completed, receiving or transfer container 22 may be sealed and separated from the system, without the introduction of air into the container. Preferably, receiving or transfer container 22 is heat sealed, although other methods of sealing are also suitable.

Other variations are encompassed by the present invention. Thus, the gas outlet may be used as a gas inlet, and, conversely, the gas inlet may be used as a gas outlet, at different stages of processing of the PC. For example, gas may be introduced and exhausted using a gas inlet and a gas outlet as described above, and the PC is recovered in a receiving or transfer container. Gas may then be introduced through the gas outlet, so that the PC remaining in the containers and/or held up in the leucocyte depletion assembly or assemblies may be collected. Of course, gas may also be introduced through the gas inlet for a similar effect.

Further embodiments are encompassed by the present invention. For example, in one embodiment, the manifold assembly 100 may comprise all of the components shown in the FIGURE, except for the leucocyte depletion assembly 32. Another embodiment of the invention may comprise all of the components shown in the FIGURE except for the gas inlet 30, the leucocyte depletion assembly 32, and the gas outlet 33. In this variation, the drip chamber 31 preferably includes a porous element for venting gas. Additionally, another embodiment of the invention may include only a single porous element interposed between the outlet of the pooling assembly 50 and the receiving or transfer container 22, which allows gas to flow therethrough. In each of these embodiments gas ahead of the flow of the PC and gas pockets moving along the conduit with the flow of PC may be prevented from entering the receiving or transfer container. Further, gas may be introduced behind the flow of PC to maximize recovery of the PC.

EXAMPLES

Example 1

The pooling assembly used to perform this example utilized six units of PC in individual 60 ml single-unit containers, and a 1500 ml storage container, set up in a manner that generally corresponds to that described for the FIGURE. The manifold assembly is arranged generally vertically, with the pooling assembly and the conduit to the receiving container having a total length of about 24 inches. Clamps on the conduits adjacent to the six single-unit containers of PC were closed, as was the clamp on the conduit between the transfer container and the gas outlet. The leucocyte depletion assembly was produced in accordance with U.S. Pat. No. 4,880,548.

A 60 cc syringe was used to introduce air through the gas inlet and into the source containers. The gas outlet was capped. The plunger of the syringe was drawn back to the "60 cc" mark, the gas inlet was uncapped, and then the syringe was connected to the gas inlet. The clamp to the first single-unit container, which contained a unit of PC, was opened, and the plunger of the syringe was pushed forward about 5–10 cc, thus introducing air into the first single-unit container. The clamp to that first container was then closed. The same procedure was followed with respect to the remaining five single-unit containers.

The syringe was then removed, the gas inlet was recapped, and the gas outlet was uncapped. The clamp to the first container was then opened to allow the PC to flow from the first container, and the drip chamber was inverted and squeezed to fill the chamber. The drip chamber was then returned to its normal orientation, and the PC flowed through the drip chamber and leucocyte depletion assembly, toward the transfer container. Air was exhausted through the opened gas outlet, until the PC contacted the liquophobic membrane in the gas outlet.

At this point, flow stopped, the clamp on the conduit leading to the transfer container was opened, and PC flowed into the transfer container.

The conduits to the other five containers were then opened sequentially, and the PC flowed out of these containers. The PC passed through the drip chamber, where the air in the system elements leading to the five containers was collected, and then the PC passed through the leucocyte depletion assembly. The flow stopped when the six containers of PC had drained.

At this point, PC remained in the leucocyte depletion assembly, the drip chamber, and the conduit downstream of the gas inlet. To recover some of this PC, the gas inlet was then uncapped, and the PC remaining in the drip chamber, conduits and half of the leucocyte depletion assembly drained into the storage container.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A system for processing biological fluid comprising:
    a pooling assembly;
    a plurality of biological fluid source containers in fluid communication with the pooling assembly;
    a receiving container in fluid communication with the pooling assembly; and
    a leucocyte depletion assembly and a gas inlet interposed between the biological fluid source containers and the receiving container.

2. The system of claim 1 further comprising a drip chamber and a gas outlet interposed between the biological fluid source containers and the receiving container.

3. The system of claim 1 comprising a closed, sterile system.

4. The system of claim 1 further comprising a gas outlet interposed between the biological fluid source containers and the receiving container.

5. The system of claim 1 comprising a closed system.

6. The system of claim 5 wherein at least one of a gas inlet, a drip chamber, a leucocyte depletion assembly, and a gas outlet is interposed between the pooling assembly and the receiving container.

7. A system for processing biological fluid comprising:
    a plurality of biological fluid source containers;
    a receiving container;
    a pooling assembly interposed between the plurality of biological fluid source containers and the receiving container, and in fluid communication with the source containers and the receiving container;
    a gas inlet interposed between the pooling assembly and the receiving container; and,
    a leukocyte depletion device interposed between the receiving container and the gas inlet.

8. The system of claim 7 further comprising a drip chamber and a gas outlet, wherein the drip chamber is interposed between the gas inlet and the leukocyte depletion device, and the gas outlet is interposed between the leukocyte depletion device and the receiving container.

* * * * *